United States Patent [19]

Webb et al.

[11] Patent Number: 4,923,807
[45] Date of Patent: May 8, 1990

[54] ARG-SERPIN HUMAN PLASMINOGEN ACTIVATOR INHIBITOR DESIGNATED PAI-2

[75] Inventors: Andrew C. Webb, Wellesley; Philip E. Auron, Framingham, both of Mass.

[73] Assignees: New England Medical Center Hospitals Inc., Boston; Tufts College, Boston; Wellesley College, Wellesley; MIT, Cambridge, all of Mass.

[21] Appl. No.: 11,580
[22] Filed: Feb. 6, 1987

Related U.S. Application Data

[63] Continuation-in-part of Ser. No. 4,319, Jan. 8, 1987, Pat. No. 4,766,069, which is a continuation of Ser. No. 611,669, May 18, 1984, abandoned.

[51] Int. Cl.$^5$ .................... C12P 21/00; C12P 21/02; C12N 5/00; C12N 1/20
[52] U.S. Cl. ................................ 435/69.2; 435/69.8; 435/240.1; 435/252.3; 435/252.33; 435/255; 435/320; 435/172.3; 536/27; 935/11; 935/69; 935/70; 935/72; 935/73
[58] Field of Search ............ 435/68, 70, 71, 91, 435/172.1, 172.3, 240.1, 240.2, 252.3, 252.31–252.35, 254, 255, 256, 320; 536/27; 530/350, 380; 935/11, 27, 70, 69, 72–75

[56] References Cited

U.S. PATENT DOCUMENTS 4,366,246 12/1982 Riggs .................... 435/68

OTHER PUBLICATIONS

Houghton et al.; Nucleic Acids Res. 8: 2885 (1980).
Okayama et al.; Molec. Cell. Biol. 3: 280 (1983).
Carrell, R. and J. Travis (1985) Trends Biolog. Sci. 10:20–24, "α$_1$-Antitrypsin and the Serpins: Variation and Countervariation".
Travis, J. and G. S. Salvesen (1983) Ann. Rev. Biochem. 52:655–709, "Human Plasma Proteinase Inhibitors".
Carrell, R. W. and M. C. Owen (1985) Nature 317:730–732, "Plakalbumin, α$_1$-Antitrypsin, Antithrombin and the Mechanism of Inflammatory Thrombosis".
Morse, J. O. (1978) New Eng. Jour. Med. 299:1045–1048, 1099–1105, "Alpha$_1$-Antitrypsin Deficiency".
Hamsten, A., Wiman, B., deFaire, U. and Blomback, M. (1985) New Eng. J. Med. 313:1557–1563, "Increased Plasma Levels of a Rapid Inhibitor of Tissue Plasminogen Activator in Young Survivors of Myocardial Infarction".
Pannekoek, H., Veerman, H., Lambers, H., Diergaarde, P., Verweij, C. L., van Zonneveld, A.-J. and van Mourik, J. A. (1986) EMBO Jour. 5:2539–2544, "Endothelial Plasminogen Activator Inhibitor (PAI): A New Member of the Serpin Gene Family".
Ginsberg, D., Zeheb, R., Yang, A. Y., Rafferty, U. M., Andreasen, P. A., Nielsen, L., Dano, K., Lebo, R. V. and Gelehrter, T. D. (1986) J. Clin. Invest. 78:1673–1680, "cDNA Cloning of Human Plasminogen Activator-Inhibitor from Endothelial Cells".
Ny, T., Sawdey, M., Lawrence, D., Millan, J. L. and Loskutoff, D. J. (1986) Proc. Natl. Acad. Sci. USA 83:6776–6780, "Cloning and Sequence of a cDNA Coding for the Human β-Migrating Endothelial-Cell-Type Plasminogen Activator Inhibitor".
Kruithof, E. K. O., Vassalli, J.-D., Schleuning, W.-D., Mattaliano, R. J. and Bachmann, F. (1986) J. Biol. Chem. 261:11207–11213, "Purification and Characterization of a Plasminogen Activator Inhibitor from the Histiocytic Lymphoma Cell Line U-937".
Scott, R. W., D. L. Eaton, N. Duran, and J. B. Baker (1983) J. Biol. Chem. 258:4397–4403, "Regulation of Extracellular Plasminogen Activator by Human Fibroblasts".

Primary Examiner—James Martinell
Attorney, Agent, or Firm—Roman Saliwanchik; David R. Saliwanchik

[57] ABSTRACT

The invention is directed to an Arg-Serpin human plasminogen activator inhibitor designated PAI-2. This protein is prepared via recombinant DNA means. The invention also includes other serpins which can be made by amino acid substitutions or deletions in conserved regions of PAI-1 and PAI-2, as shown in FIG. 4. The proteins of the invention can be used to inhibit, or at least modulate, human plasminogen activator activity in a variety of physiological conditions, e.g., fibrinolysis, tumor metastasis, and tumor growth.

13 Claims, 7 Drawing Sheets

```
                                                                                                                                                    830
    730                 750                 770                 790                 810
    AATGGGCTTTATCCTTTCCGTGTAAACTCGGCTCAGCGCACACCTGTACAGATGATGCTTGCGTGAAAAGCTAAACATTGGATACATAGAAGACCTAAAGGCTCAGATTCTAGAACTC
217 AsnGlyLeuTyrProPheArgValAsnSerAlaGlnArgThrProValGlnMetMetTyrLeuArgGluLysLeuAsnIleGlyTyrIleGluAspLeuLysAlaGlnIleLeuGluLeu 850                 870                 890                 910                 930                 950
    CCATATGCTGGAGATGTTAGCATGTTCTTGTTGCTTCCAGATGAAATTGCCGATGTGTCCACTGGCTTGGAGCTGCTGGAAAGTGAAATAACCTATGACAAACTCAACAAGTGGACCAGC
257 ProTyrAlaGlyAspValSerMetPheLeuLeuLeuProAspGluIleAlaAspValSerThrGlyLeuGluLeuLeuGluSerGluIleThrTyrAspLysLeuAsnLysTrpThrSer 990                 1010                1030                1050                1070
    AAAGACAAAATGGCTGAAGATGAAGTTGAGGTATACATACCCAGTTCAAATTAGAAGAGCATTATGAACTTCAGATCCATTCTGAGAAGCATGGGCATGGTGAATGAGAGGCACTGAACAGGGA
297 LysAspLysMetAlaGluAspGluValGluValTyrIleProGlnPheLysLeuGluGluHisTyrGluLeuArgSerMetGlyMetGluAspAlaPheAsnLysGly 1090                1110                1130                1150                1170                1190
    CGGGCCAATTTCTCAGGATGCTGGGAGAGGAATGACCTGTTTCTTCTTCGAAGTGTTCCACCAAGCCATGGATGGAATGAGGAGGGCACTGCTGAAGCAGCCGCTGCCACAGGAGGTGTT
337 ArgAlaAsnPheSerGlyMetSerGluArgAsnAspLeuPheLeuSerGluValPheHisGlnAlaMetValAspValAsnGluGluThrGluAlaAlaGlyThrGlyGlyVal
    *

1250                1270                1290                1310
    ATGACAGGAGAACTGGACATGAGGGCCACAGTTGTGGCAGATCATCCTTTCTTTTTCTTATTATGCATAAGATAACCAACTGCATTTATTTTCGGCAGATTTCCTCACCCTAA
377 MetThrGlyArgThrGlyHisSerGlyTyrProGlnPheValAlaAspHisProPheLeuPheLeuIleMetHisLysIleThrAsnCysIleLeuPheLeuPheGlyArgPheSerSerProEnd
    ⇦
```

FIGURE 3A cont.

```
       1330              1350              1370              1390              1410              1430
AACTAAGCGTGCTTCTGCAAAAGATTTTTGTAGATGAGCTGTGCCTCAGAATTGCTATTCAAATTGCCAAAAATTTAGAGATGTTTTCTACATATTTCTGCTCTTCTGAACAAC 1450              1470              1490              1510              1530              1550
TTCTGCTACCCACTAAATAAAACACAGAAATAATTAGACAAATTGTCTATTATATAACATGACAACCCTATTAATCATTGGTCTTCTAAAATGGGATCATGCCATTTAGATTTTCCTTAC 1570              1590              1610              1630              1650              1670
TATCAG[TATTTTTTA]AACATTAACTTTACTTTG[TATTTATTATT]TATATAATGGTGAGTTTTAAATTATTGCTCACTGCC[TATTTAA]TGTAGCTAATAAAGTTATAGAAGCAGA 1690              1710              1730              1750              1770              1790
TGATCTGTTAATTTCCTATCTAATAAATGCCTTTAATTGTTCTCATAATGAAGAATAAGTAGGTACCCTCCATGCCCTTCTGTAATAAATATCTGGAAAAACATTAAACAATAGGCAAA 1810              1830              1850              1870              1890              1910
TATATGTTATGTGCATTTCTAGAAATACATAACACATATATGTCTGTATCTTATATTCAATTGCAAGTATATAATAAATAAACCTGCTTCCAAACAACAACAAAAAAAAAAAAAAAAAA
```

FIGURE 4

```
PAI-1:  .....VQRDLKLV----QGFMPHFFRL---FRSDVKQVDFSE-VERARF-I-NDWVK-THTK
MAS:    .....LESVNKLFGEKSASFREEYIRLCQKYYSSEPQAVDFLECAEE-ARKK-I-NSWVKTQTK
ATIII:  .....LVSANRLFGDKSLTFNETYQDISELVYGAKLQPLDFKENAEQSRAAINKWVSNKTE
API:    .....LTTDGGLFLSEGLKLVDKFLEDVKKLYHSEAFTVNFGD-TEEAKKQINDYVEKGTQ

PAI-1:  GM-ISNLLGKGAVDQLTRLVLVNALYFNGQWKTPFPDSSTHRRL---EKKLNGLYPFRVNSAQRTPVQMM--HWVKTQMM
MAS:    GK-IPNLLPEGSVDGDTRMVLVNAVYFKGKWKTPF---EKKLNGLYPFRVNSAQRTPVQMM--HWVKTQMM
ATIII:  GRITDVIPSEAINELTVLVLVNTIYFKGLWKSKFSP---ENTRKELF-YKADG-ESCSASMM
API:    GKIVDLV-KE-LDRDTVFALVNYIFFKGKWERPF----EVKDTEEEDFHVDQVTTVKVPMM
```

FIGURE 4 continued

```
PAI-1:  AQTNK FN   Y    TE  FTTPDGHYYD ILELPY HGDT LSMF I AA  YE  KE VP   L SA L TNILS
MAS:          LN   GY    E  EDLKA               ILELPY AGD  VSMF     PDE IA DV STG LE LL SE I T
ATIII:  YQEGKFR    YRRVAE GT          QVLELPFKGDDITMVLILPK P         EKSLAKVEKELT
API:    KRLGMFNIQH   CKKLSS           WVLLMKYLGN ANAIFFLPDE           GKLQHLENELT

PAI-1:  AQLISHW    KGN MTRLPRLLVL PK F SL  E TEVDL RK PL EN LG MT DMF RQ F QAD F TS L       S    S
MAS:    YDKLNKWT   SK D KM AEDEVEVY I PQ F KL  E EHYE LRS  I L RS MG ME DA FNKGR AN FSGM    S    S
ATIII:  PEVLQEWL   DELEEMMLVVHMPRFRIEDGFSLKEQLQDMGLVDLFSPEKSKLPGIVAE
API:    HDIITKFLENEDRRSASLHL  PKLSITGTYDLKSVLGQLGITKVFSNG ADLSGV TE
```

FIGURE 4 cont.

```
PAI-1:  D Q E P L H V A Q A L Q K V K I E V N E S G T V A S S S T A V I V S A R M A P E - - - E I I M D R P F L F V V R H N P T
MAS:    E R N D L F L S E V F H Q A M V D V N E E G T E A A A G T G G V M T G R T G H G G P - Q F V A D H P F L F L I M H K I T
AT III: G R D D L Y V S D A F H K A F L E V N E E G S E A A A S T A V V I A G R S L N P N R V T F K A N R P F L V F I R E V P L
API:    E A P - L K L S K A V H K A V L T I D E K G T E A A G A M F L E A I P M S I - - - P P E V K F N K P F V F L M I E Q N T

↙ P₁

PAI-1:  G T V L F M G Q V M E P - COOH
MAS:    N C I L F F G R F S S P - COOH
AT III: N T I I F M G R V A N P C V K - COOH
API:    K S P L F M G K V V N P T Q K - COOH
```

| | Align Scores (SD) | | | | % homology | | |
|---|---|---|---|---|---|---|---|
| | PAI-1 | MAS | AT III | | PAI-1 | MAS | AT III |
| MAS: | 19.17 | | | | 35.8 | | |
| AT III: | 20.29 | 22.45 | | | 31.7 | 36.6 | |
| API: | 20.99 | 16.79 | 19.64 | | 32.9 | 34.4 | 31.2 |

ARG-SERPIN HUMAN PLASMINOGEN ACTIVATOR INHIBITOR DESIGNATED PAI-2

This is a continuation-in-part of our copending patent application Ser. No. 004,319, filed Jan. 8, 1987, now U.S. Pat. No. 4,766,069, which is a continuation of application Ser. No. 611,669, filed May 18, 1984, now abandoned.

BACKGROUND OF THE INVENTION

The phagocytic cells of the peripheral blood mononuclear population are a major source of potent serine proteases that play essential roles in the pathophysiology of tissue homeostasis, inflammation and blood coagulation. The neutral proteases secreted by stimulated monocytes/macrophages include elastase, plasminogen-activators, and collagenases, as well as components of both the coagulation and complement pathways. In addition to contributing to the structural reorganization of tissue, particularly at inflammatory sites, some of these proteases also appear to be instrumental in the control of mononuclear cell and tumor cell migration and both the cytolytic and mitogenic activities of macrophages.

The mechanism universally employed to regulate the destructive effects of serine proteases is the coordinated synthesis of specific endogenous inhibitors. These serine protease inhibitors constitute a family of closely related and structurally highly conserved proteins (the Serpin superfamily [Carrell, R. and Travis, J. (1985) Trends Biol. Sci. 10:20–24]), with the common functional feature that they "trap" the protease by presenting a reactive site that provides an "ideal" pseudo-substrate (Travis, J. and Salvesen G. S. [1983] Ann. Rev. Biochem. 52:655–709). The target specificity of each Serpin (i.e., Met or Val for elastase; Leu for chymase; Arg for thrombin) is determined by the amino acid residue located at its reactive center, which is normally the same amino acid found on the amino-terminal side of the peptide bond to be cleaved by the protease in the legitimate substrate (Travis and Salveson, supra). This crucial amino acid forms the basis for a Serpin classification scheme (e.g., Met-Serpin, Arg-Serpin, etc. [Carrell, R. and Travis, J. (1985), supra]. The enzyme and its inhibitor bind tenaciously to form a complex that is typically stable to boiling in detergent, but is susceptible to neutrophilic cleavage with ammonium hydroxide. Failure or lack of regulation of these powerful proteolytic enzymes is known to lead to severe pathological effects (Carrell and Travis, supra; Carrell, R. W. and Owen, M. C. [1985] Nature 317:730–732). For example, a genetic or environmentally induced deficiency in the most prevalent serum Met-Serpin, $\alpha_1$-protease inhibitor (API), has been demonstrated to account for the loss of pulmonary function associated with emphysema (Morse, J. O. [1978] N. Engl. J. Med. 299:1099–1105). Conversely, an overproduction of the Arg-Serpin that inhibits the action of the plasminogen activator (PA) found in plasma, has been correlated with human thromboembolic disease (Hamsten, A., Wiman, B., de Faire, U. and Blomback, M. [1985] N. Eng. J. Med. 313:1557–1563).

An endothelial cell plasminogen activator inhibitor (PAI-1) clone was recently reported (Pannekoek, H., Veerman, H., Lambers, H., Diergaarde, P., Verweij, C. L., van Zonneveld, A.-J. and van Mourik, J. A. [1986] EMBO Jour. 5:2539–2544; Ginsburg, D., Zeheb, R., Yang, A. Y., Rafferty, U. M., Andreasen, P. A., Nielsen, L., Dano, K., Lebo, R. V. and Gelehrter, T. D. [1986] J. Clin. Invest. 78:1673–1680; Ny, T., Sawdey, M., Lawrence, D., Millan, J. L. and Loskutoff, D. J. [1986] Proc. Natl. Acad. Sci. USA 83:6776–6780). This is distinctly different from the monocyte-derived cDNA coding for PAI-2, the subject of this invention.

A recently published (Kruithof, E. K. O., Vassalli, J.-D., Schleuning, W.-D., Mattaliano, R. J. and Bachmann, F. [1986] J. Biol. Chem. 261:11207–11213) partial amino acid sequence (30 carboxyl residues) of monocyte-derived PAI-2 was found to exactly match residues 347–376 (boxed in FIG. 3A) of the amino acid sequence deduced from our clone pcD-1214. Perfect homology over 30 amino acid residues strongly suggests that the monocyte Arg-Serpin identified in this is the same protein isolated and characterized biochemically from U937 cells by Kruithof et al., and now classified as PAI-2 (Kruithof et al., supra). Northern blots of mRNA from stimulated U937 cells probed with the monocyte Arg-Serpin clone confirm transcriptional activity of this gene in these cells (FIG. 2; lane 5).

Monocyte PAI (PAI-2) is synthesized upon stimulation of monocytes/macrophages with lipopolysaccharide (LPS), phorbol ester (PMA), or muramyl dipeptide (MDP). The biochemical properties of the PAI-2 distinguish it from both protease-nexin secreted by fibroblasts (Scott, R. W., Eaton, D. L., Duran, N. and Baker, J. B. [1983] J. Biol. Chem. 258:4397–4403) and the endothelial cellderived PAI-1(Pannekoek et al. supra).

BRIEF SUMMARY OF THE INVENTION

Disclosed and claimed is an Arg-Serpin human plasminogen activator inhibitor designated PAI-2. This precursor polypeptide has a predicted 415 amino acids sequence (Table A), with a calculated molecular weight of 46,596 and a ~35% homology with members of the serine protease inhibitor (Serpin) superfamily. By homology with other secreted polypeptides, it is predicted that a 22 amino acid residue signal peptide is cleaved from the Arg-Serpin to yield a 43,000 kilodalton (kD) mature protein (Table B).

PAI-2 is expressed by a gene located on clone pcD-1214. The nucleotide sequence (DNA) of the gene encoding PAI-2 has been prepared in its essentially pure form substantially free of other DNA.

The gene for PAI-2 has been mapped to human chromosome 18 by Southern blot analysis of human-mouse somatic cell hybrid DNAs. As a naturally occurring regulator of plasmin-mediated proteolysis via inhibition of plasminogen-activator (PA), this monocyte-derived Arg-Serpin may have utility as a substitute for $\epsilon$-aminocaproic acid (EACA) in the therapeutic modulation of fibrinolysis as well as in the inhibition of tumor cell infiltration and metastasis.

DESCRIPTION OF THE DRAWINGS

FIG. 3A: Nucleotide sequence of plasmid pcD-1214 cDNA 1900 bp insert (nucleotides numbered above the lines). The 415 amino acid polypeptide encoded by this sequence is indicated by three-letter code (amino acids numbered down left margin). Cysteine residues are capitalized (CYS) and potential N-linked glycosylation sites are shown by an asterisk(*). The solid arrowhead between $Ala_{22}$ and $Ser_{23}$ represents the proposed cleavage site for the signal peptide and the putative reactive center ($P_1$ residue) $Arg_{380}$ for this Serpin is indicated with a broad, open arrow. The 30 carboxyl amino acids (residues 347–376) that match the recently published (Kruithof et al., supra) sequence of the tryptic peptide from PAI-2 are boxed. Nucleotide sequences of interest are highlighted as follows: 5' translational terminators-overlined; polyadenylation signals-underlined; 3' AT-rich repeats-boxed.

FIG. 4: Computer alignment of the carboxyl-terminal segments of selected Serpin polypeptides (subscript-number of amino acids in each protein). Perfectly matched amino acids are indicated by a vertical line and regions of structurally similar amino acids are boxed. The reactive center $P_1$ residue that is crucial for substrate specificity and classifies each Serpin is indicated by an arrow. The degree of relatedness of these Serpins is indicated by tabulation of data (both Align Scores and % amino acid homology) obtained by use of the ALIGN algorithm. Key: PAI-1-endothelial cell plasminogen-activator inhibitor; MAS-monocyte Arg-Serpin; ATIII-antithrombin III; API-$\alpha_1$-protease inhibitor.

DESCRIPTION OF THE TABLES

Table A: Amino Acid Sequence of Precursor PAI-2
Table B: Amino Acid Sequence of Mature PAI-2
Table C: Nucleotide Sequence of Monocyte cDNA pcD-1214
Table D: Nucleotide Sequence and Deduced Amino Acid Sequence of pcD-1214

DETAILED DISCLOSURE OF THE INVENTION

The following deposit of the culture disclosed in this application has been made in the Agricultural Research Culture Collection (NRRL), Northern Regional Research Center, U.S. Department of Agriculture, 1815 North University Street, Peoria, Ill. 61604, U.S.A.

| Culture | Repository No. | Deposit Date |
|---|---|---|
| E. coli HB101 (pcD-1214) | NRRL B-18161 | Jan. 14, 1987 |

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Figure 6:
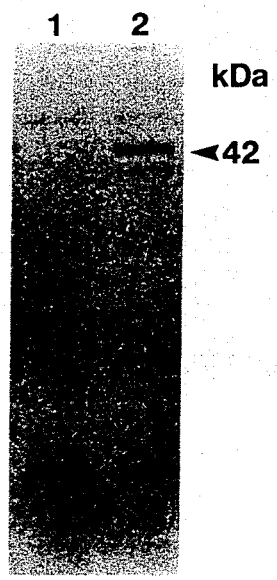
FIG. 6: In vitro translation of monocyte Arg-Serpin. RNA transcripts of pcD-1214 were made in vitro with SP6 polymerase were added to reticulocyte lysate containing [$^{35}$S]-methionine. The translation products were visualized by fluorography after fractionation on a 17.5% polyacrylamide gel. The position of barley α-amylase (42 kD) migrated in an adjacent lane provides a molecular weight marker. Lane 1: distilled water control; Lane 2: 750 ng pcD-1214ΔDX RNA transcript.

Nucleotide sequencing of the stimulation-specific clone pcD-1214 isolated from an LPS-stimulated, human monocyte cDNA library revealed an open reading frame (ORF) coding for the precursor to a secreted polypeptide of 415 amino acids with a calculated molecular weight of 45.6 kD and a 22 residue signal peptide sequence. The ligitimacy of this reading frame was established by reticulocyte lysate translation of SP6-generated cDNA transcripts to yield a polypeptide with an apparent molecular mass ($M_r$) of 42,000 in SDS-polyacrylamide gels (FIG. 6). Alignment of the predicted amino acid sequence with the sequences of other proteins recorded in the National Biomedical Research Foundation (NBRF) database, or others recently published (Ny et al. and Ginsburg et al., supra) identified this human monocyte product as being a member of the Serpin (anti-protease) superfamily. The highest degree of homology between the Serpins is generally found within the hydrophobic regions located at the carboxyl-termini, particularly around the reaction center that determines "target" specificity. Taking advantage of this homology to optimize alignment, the monocyte Serpin was found to possess an arginine ($Arg_{380}$) residue within the reactive center at the crucial $P_1$ position. This feature places this monocyte anti-protease within the Arg-Serpin subgroup, which includes antithrombin III (ATIII) and the plasminogen-activator inhibitor derived from endothelial cells (PAI-1). In common with all Serpins sequenced to date, the "hinge" residue at $P_{17}$ is glutamic acid (Carrell et al., supra). Both overall amino acid homology and alignment scores (see tables in FIG. 4) suggest that the monocyte Arg-Serpin (MAS) is marginally more closely related to ATIII than to PAI-1.

The assignment of the monocyte Arg-Serpin gene to human chromosome 18 provides a useful marker on a relatively poorly mapped chromosome in the genome and establishes a firm genetic basis for the study of inherited deficiencies in this gene that might be manifested clinically as various fibrinolytic, thrombolytic, inflammatory and even metastatic conditions (Kruithof, E. K. O., Gudinchet, A., Tran-Thang, C., Ransijn, A. and Bachmann, F. [1985] in Progress in Fibrinolysis, 7:130–132) resulting from unrestricted release of plasmin by PA. Recently the PAI-1 gene was reported to be located on human chromosome 7 (Ginsburg et al., supra). The other Serpins mapped to date include: ATIII to the long arm of chromosome 1 (1q23–q25), API and $\alpha_1$-antichymotrypsin to the long arm of chromosome 14 (14q31–q32), and a recently recognized anti-protease, thyroxinebinding globulin on the long arm of the X chromosome. The urokinase-type plasminogen activator (u-PA) gene has been localized to 10q24-qter, whereas the tissue-type (t-PA) gene is on chromosome 8p12.

Figure 2:
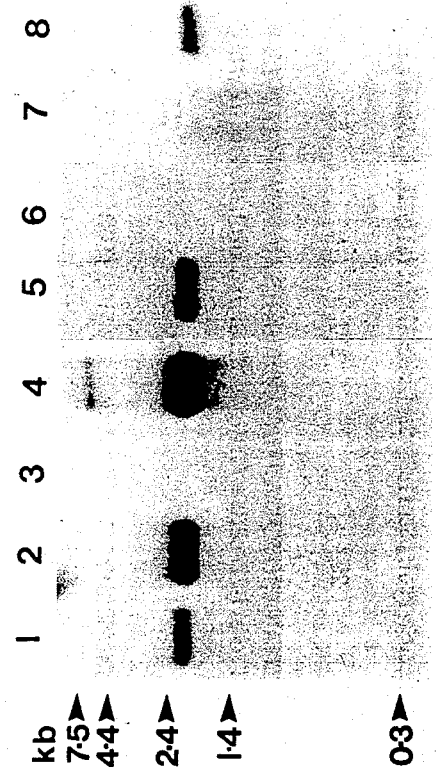
FIG. 2: Northern blot analysis of expression of pcD-1214 mRNA by different cell types in response to stimulation. All RNA samples are poly(A)+ with the exception of Lanes 3 and 7. Lane 1: 100 ng 12 hr LPS-stimulated monocyte; Lane 2: 100 ng 4 hr adhered monocyte; Lane 3: 1 μg unstimulated monocyte; Lane 4: 100 ng 4 hr LPS-stimulated monocyte; Lane 5: 100 ng TSST-1-stimulated U937 cell; Lane 6: 100 ng Colo16 keratinocyte cell; Lane 7: 10 μg unstimulated endothelial cell; Lane 8: 30 ng LPS-stimulated endothelial cell. Nucleotide lengths indicated in left margin are derived from RNA ladder (BRL-Gibco) migrated in parallel lanes of same gel.

The monocytic Arg-Serpin gene appears to be very active in endothelial cells after stimulation with LPS (FIG. 2; Lanes 7 and 8). This is in contrast to the PAI-1 which has been found to be synthesized constitutively by these cells. The possibility that both PAI-1 and PAI-2 are synthesized by endothelial cells may warrant a reassessment of the relative importance of PAI-1 and PAI-2 in endothelial cell control of fibrinolysis and localized vasculitis associated with tumor cell penetration. In some respects PAI-2 could be considered a physiologically more viable candidate for modulation of intravascular PA activity than PAI-1. For example, PAI-1 is secreted by endothelial cells as a latent inhibitor that can only be activated in vitro by treatment with SDS and presumably also requires some cofactor in vivo to achieve full biological activity. The extent to which PAI-2 gene expression is under similar mechanisms of control in both monocytic and endothelial cells is now a major focus of our attention.

Following are examples which illustrate procedures for practicing the invention. These examples should not be construed as limiting. All percentages are by weight and all solvent mixture proportions are by volume unless otherwise noted.

EXAMPLE 1

Molecular cloning of human monocyte cDNA library

Figure 1:
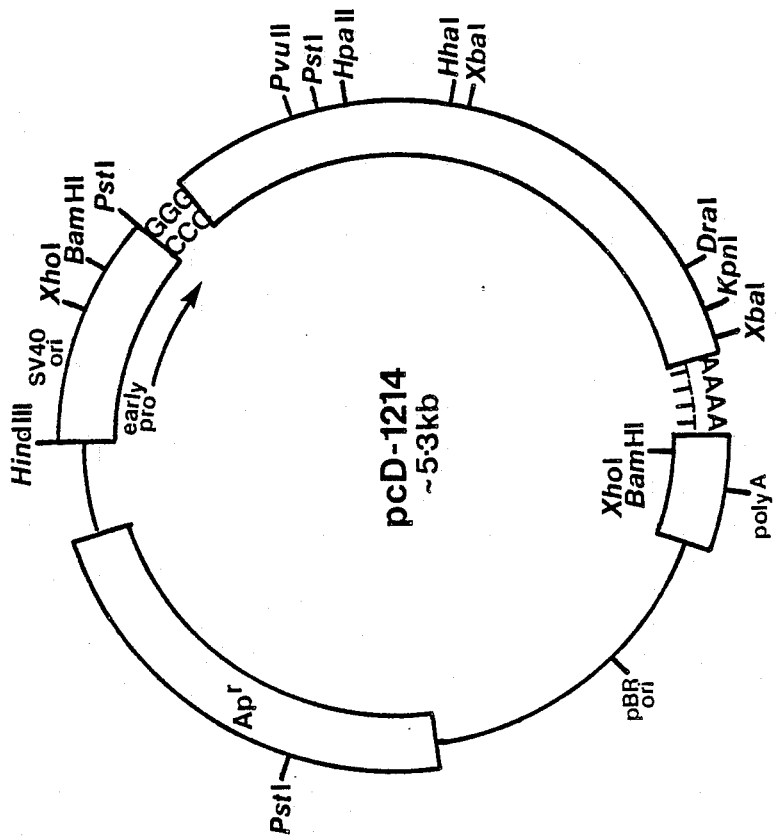
FIG. 1: Restriction map (not to scale) of cDNA clone pcD-1214 isolated from an LPS-stimulated, human monocyte library constructed in the Okayama and Berg expression vector. Only sites for restriction enzymes that cleave once or twice within the cDNA insert (solid box) are indicated. Portions of the shuttle vector derived from SV40 (shaded) are distinguished from the pBR322 segments (line and open box).

The preparation of our cDNA library from poly(A)+ isolated from LPS stimulated human peripheral blood monocytes is described in detail elsewhere (Auron, P. E., Webb, A. C., Rosenwasser, L. J., Mucci, S. F., Rich, A., Wolff, S. M. and Dinarello, C. A. [1984] Proc. Natl. Acad. Sci. U.S.A. 81:7907–7911; Webb, A. C., Auron, P. E., Rich, A., Rosenwasser, L. J., Wolff, S. M. and Dinarello, C. A. [1985] in Cellular and Molecular Biology of Lymphokines, Sorg, C. and Schimpl, A. Ed., pp. 685–695, Academic Press, N.Y). The clone pcD-1214 (FIG. 1) carried in the Okayama-Berg expression vector (Okayama, H. and Berg, P. [1983] Molec. Cell. Biol. 3:280–289) was characterized as harboring an approximately 2 kilobase pair (kbp) cDNA insert coding for a stimulation-specific mRNA, by virtue of its hybridization exclusively to cDNA probes made from stimulated monocyte poly(A)+ RNA. This clone, pcD-1214, was used as a negative control during characterization of the cDNA for interleukin-1β (IL-1β) from this same library (Auron et al. supra).

The cloning and expression of the PAI-2 gene was accomplished by use of a modified Okayama-Berg (Okayama, H. and Berg, P. [1982] Mol. and Cell. Biol. 2:161–170) protocol. The first modification concerned the use of E. coli DNA polymerase I for second stranding after RNase H removal of the template mRNA. The Okayama and Berg procedure utilized a non-commercial enzyme from a private source. Our attempt at using commercially available (nuclease-free) DNA polymerase I holoenzyme treated with subtilisin to derive the large fragment (Klenow fragment) resulted in an incompletely replaced DNA second strand. This incomplete and mixed RNA-DNA duplex led to severe deletions following transformation into E. coli strain HB101. This was presumably due to a lack of 3'→5' exonuclease activity required for complete removal of RNA fragments remaining following ribonuclease H digestion. The second-strand synthesis part of the technique only worked following the availability of endonuclease-free commercial preparations of DNA polymerase I by companies such as Boehringer Mannheim at the end of 1982, approximately nine months after the publication of the Okayama-Berg procedure.

The second modification was made to overcome the non-reproducibility of yield associated with the preparation of the vector linker fragment. The original procedure described by Okayama and Berg resulted in an extremely low yield of oligo G-tailed linker, which rendered the system very inefficient. We discovered that the problem of low yield related to the aggregation of the linker sequence into large molecular weight forms following ethanol precipitation, probably resulting from intermolecular base-pairing with the long oligo-G tails added to the linker as directed by the original Okayama-Berg procedure (Mol. Cell. Biol. 2:161–170 [1982]. Our modified procedure involved disaggregating the linker prior to agarose gel purification. Simply put, the linker (following tailing and the final restriction endonuclease HindIII digestion) was heated 10 min at 67° C. in low salt (10 mM Tris-Cl, pH 7.6; 1 mM EDTA) buffer for 3 min, slow cooled at 25° C. for 15 min and then applied to an agarose gel for electrophoretic purification. This procedure yielded a 100-fold higher yield of functional linker and permitted us to use the remainder of the Okayama-Berg procedure successfully.

EXAMPLE 2

Sequencing and analysis

Fragments of the pcD-1214 cDNA were subcloned into M13 vectors in preparation for DNA sequencing by the dideoxynucleotide chain termination method (Sanger., F., Nicklen, S. and Coulson, A. R. [1977] Proc. Natl. Acad. Sci. U.S.A. 74:5463–5467). Two different sequencing strategies were undertaken, both employing [$\alpha$-$^{35}$S]-dATP (NEN-DuPont) as the isotopic tracer and a universal primer. The first approach used a 2.3 kbp XhoI fragment (FIG. 1) which was either subcloned intact into SalI digested M13 mp 9, or digested with a variety of restriction endonucleases to generate convenient sub-fragments for both sequencing and subcloning into appropriately digested M13 mp 8 or M13 mp 9 vectors. These subclones were carried in the E. coli host JM103 (Messing, J. [1983] Meth. Enzymol. 101:20-78).

The second approach utilized the deletion subcloning method of Dale et al. (Dale, R. M. K., McClure, B. A. and Houchins, J. P. [1985] Plasmid 13:31-40). Two M13 mp 9 subclones containing the entire pcD-1214 XhoI fragment cloned in opposite orientations were used to generate single-stranded phage DNA which was linearized by EcoRI digestion of the template annealed to an oligonucleotide (RD22 from International Biotechnology, New Haven, Conn.) spanning the EcoRI site in the M13 mp 9 polylinker region. A series of overlapping deletions on each strand of the pcD-1214 cDNA were created precisely as described in the International Biotechnology Cyclone Manual. (Protocal cited in Dale, R. M. K., McClure, B. A. and Houchins, J. P. [1985] Plasmid 13:31-40.) Competent E. coli JM101 were transformed with pooled samples of deleted template DNA. Clones were selected for DNA sequencing based upon estimates of their insert size obtained by direct electrophoresis of phage template DNA on 0.7% agarose gels. Single-stranded DNA prepared from M13 mp 9 vector without an insert and M13 mp 9 containing an undeleted pcD-1214 XhoI fragment served as molecular weight markers.

Nucleotide sequence obtained from the M13 subclones generated as described above was assembled using the DB system described by Staden (Staden, R. [1984] Nucl. Acids Res. 12:499-503). Subsequent computer analysis of the completed sequence was performed using a variety of software from both The University of Wisconsin Genetics Computer Group (UWGCG) and National Biomedical Research Foundation (NBRF) packages.

EXAMPLE 3

Northern blot analysis

Poly(A)+ RNA isolated from guanidinium isothiocyanate (GTC) extracted human monocytes as described previously (Auron et al. supra) was fractionated on 1.5% formaldehyde-agarose gels (Saman, E. [1986] Gene Anal. Techn. 3:1-5), electro-blotted to Genescreen membranes (DuPont-NEN), and hybridized in the presence of 50% formamide-10% dextran sulphate with a 1256 bp PstI-DraI pcD-1214 fragment (FIGS. 1 and 3B) according to the protocol developed for use with GENESCREEN by the manufacturer. The cDNA probe was isolated and nick-translated using established procedures. Samples (1 μg) of the BRL-Gibco RNA ladder were run in adjacent lanes on the same gel for use as molecular weight markers. These standards were visualized after blotting by staining the GENESCREEN strips with ferri-dye (Saman, E. [1986] Gene Anal. Techn. 3:1-5).

EXAMPLE 4

Chromosomal assignment

The gene complementary to the pcD-1214 cDNA sequence was assigned to a particular human chromosome by Southern blot analysis of mouse-human somatic cell hybrid genomic DNA as described previously (Webb, A. C., Collins, K. L., Auron, P. E., Eddy, R. L., Nakai, H., Byers, M. G., Haley, L. L., Henry, W. M. and Shows, T. B. [1986] Lymphokine Res. 5:77-85). A panel of hybrid cell lines was obtained, selected and evaluated for their human chromosomal content as published (Shows, T. B., Sakaguchi, A. Y. and Naylor, S. L. [1982] in Adv. Human Genet., Harris, H. and Hirschhorn, K., Ed., pp. 341-452, Plenum Press, N.Y.). Human, mouse and hybrid genomic DNAs were digested with BglII, fractionated by electrophoresis in 0.7% agarose gels and blotted to GENESCREEN membranes. These blots were also probed with the internal 1256 bp PstI-DraI fragment isolated from the pcD-1214 plasmid and nick-translated in the presence of $[\alpha^{32}P]$-dCTP (NEN-DuPont) to $> 10^8$ cpm/μg by conventional techniques. The conditions for membrane hybridization, washing and autoradiography were all as described previously (Webb et al. [1986] Lymphokine Res., supra).

EXAMPLE 5

In vitro translation

The pcD-1214 cDNA insert was subcloned as a 3' truncated, 1.63 kbp PstI-DraI fragment (FIGS. 1 and 3B) into the expression vector pSP64 (Promega Biotech) polylinker region in preparation for in vitro transcription utilizing EcoRI linearized template plasmid DNA and SP6 RNA polymerase (Promega Biotech) as described by the manufacturer. Uncapped RNA transcripts were translated in a rabbit reticulocyte lysate in the presence of $[^{35}S]$-methionine (NEN-DuPont) and analyzed by SDS-PAGE as previously described (Auron et al. supra).

EXAMPLE 6

Characterization of the stimulation-specific clone pcD-1214

Restriction enzyme analysis of pcD-1214 plasmid revealed a cDNA insert of about 2 kb in length. Characterization of the mRNA complementary to the pcD-1214 insert by Northern blot hybridization to monocyte poly(A)+ RNA revealed a single species of mRNA about 2,000 nucleotides (nt) in length, the expression of which is clearly initiated by stimulation (either adherence or LPS) of human monocytes (FIG. 2; lanes 1-4). From this initial analysis, it appeared that the pcD-1214 insert was probably a full-length copy of the template mRNA. A minor, higher molecular weight RNA (approximately 6 kb) that hybridizes to the pcD-1214 probe was seen in samples containing relatively more 2 kb mRNA (e.g., FIG. 2; lane 4). Since the poly(A)+ RNA preparation used in this study was prepared from GTC cell lysates, this high molecular weight species may represent a stable (hnRNA) splicing intermediate.

A preliminary survey of pcD-1214 gene expression in IL-1 producing cells by Northern blot analysis revealed that transcription of this gene is linked to cellular stimulation. For example, endothelial cells from human umbilical vein synthesize appreciable amounts of pcD-1214 mRNA only when stimulated with LPS (FIG. 2; lanes 7 and 8). Similarly, cells of the histiocytic lymphoma cell line U937 activate the pcD-1214 gene on exposure to toxic shock syndrome toxin (FIG. 2; lane 5), whereas the keratinocyte line Colo16 (FIG. 2; lane 6), which is a constitutive producer of IL-1 (ETAF) (Sauder, D. N. [1985] in The Physiologic, Metabolic, and Immunologic Actions of Interleukin-1, Kluger, M. J., Oppenheim, J. J. and Powanda, M. C., Ed. pp. 365–373, Alan R. Liss, Inc., N.Y.) does not transcribe the pcD-1214 gene.

The precise kinetics of expression of the pcD-1214 gene in monocytic cells are presently under investigation, but preliminary data from nuclear run-off experiments in the monocytic leukemia line THP-1 indicate that, in common with the IL-1β gene, the pcD-1214 gene may undergo transient expression of the type found in association with many oncogenes and "competence factors" (Mitchell, R. L., Zokas, L., Schreiber, R. D. and Verma, I. M. [1985] Cell 40:209–217). This conclusion is consistent with the Northern blot data presented in FIG. 1, which indicate that the levels of pcD-1214 mRNA in peripheral blood monocytes 4 hr after LPS-stimulation (lane 4) are considerably higher than seen at 12 hr following stimulation (lane 1).

EXAMPLE 7

Nucleotide sequence of monocyte cDNA pcD-1214

Figure 3A:
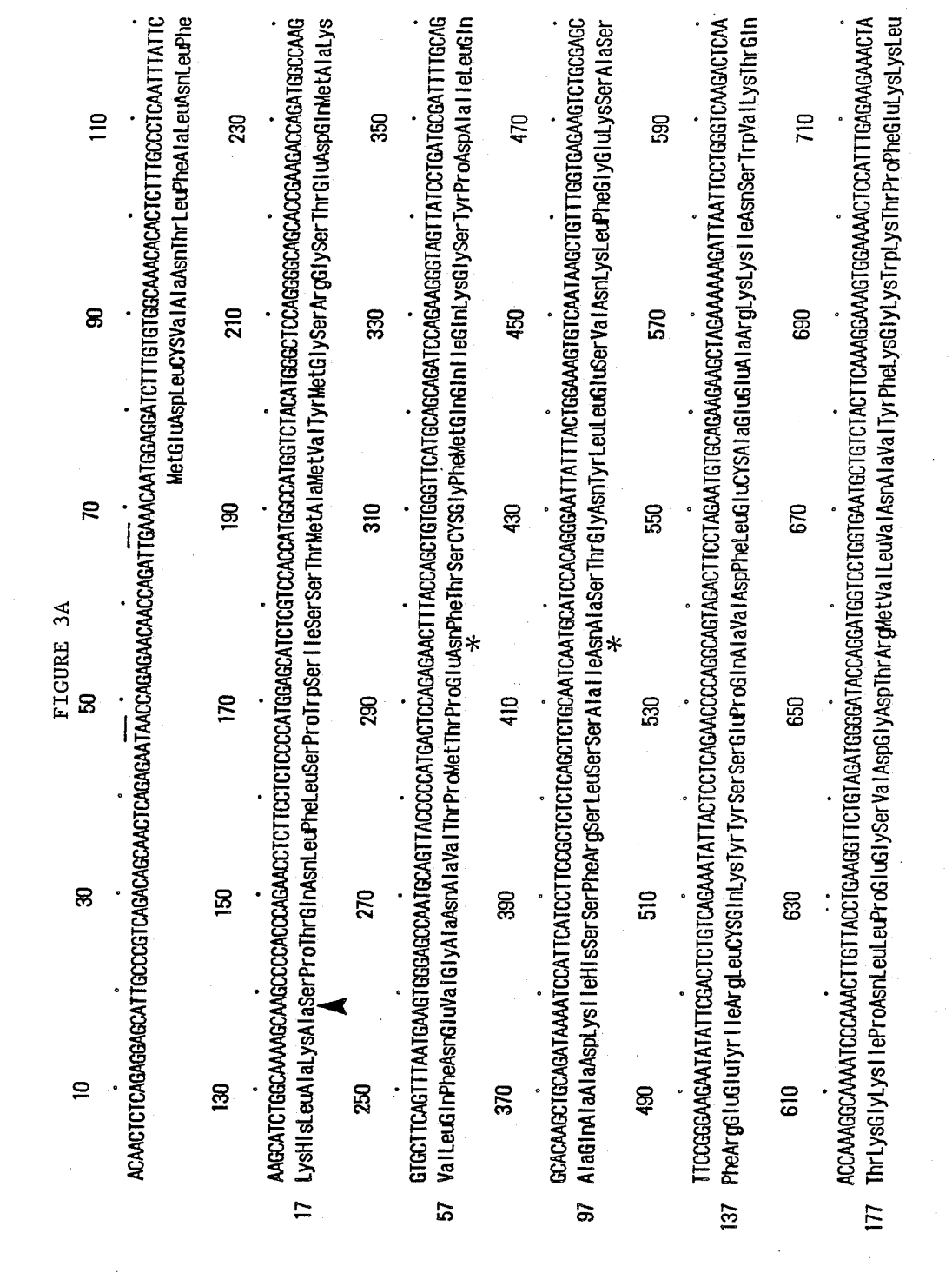
Figure 3B:
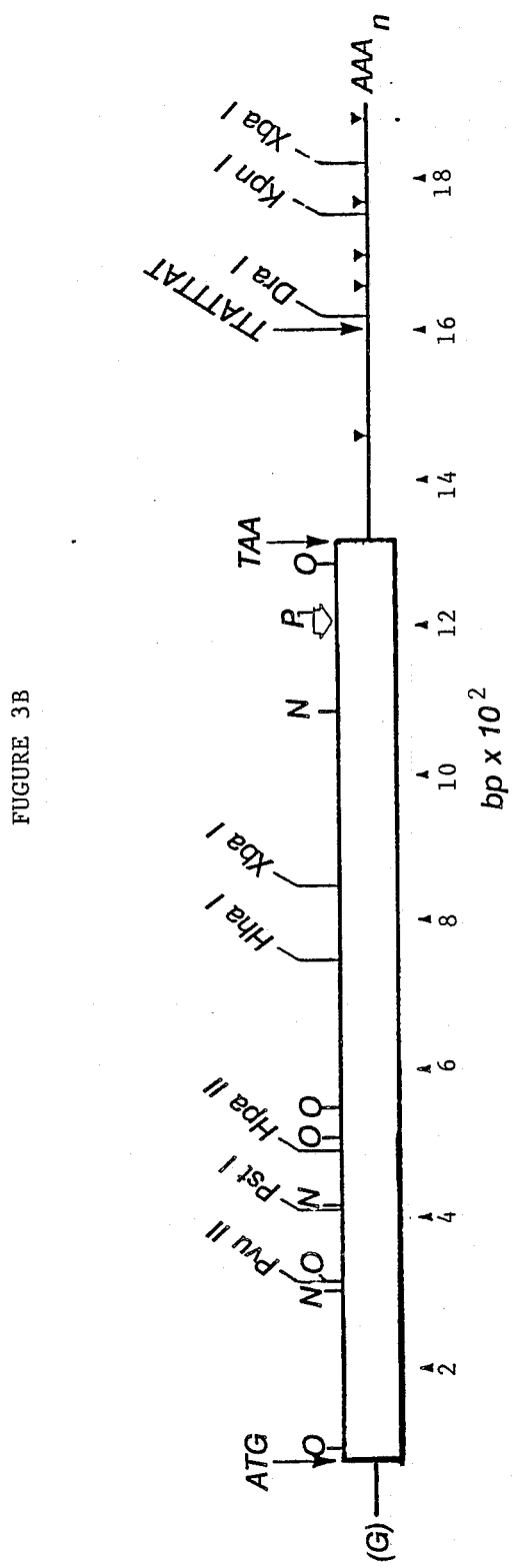
FIG. 3B: Restriction map of pcD-1214 cDNA indicating relative positions of rare restriction enzyme sites, the open reading frame (ORF) (shaded box), cysteine residues (O), asparaginelinked glycosylation sites (N), putative Serpin $P_1$ reactive center ◇, polyadenylation signal sequences ▼ and conserved 3' untranslated AT-rich sequence (TTATTTAT).

Dideoxynucleotide sequencing of the pcD-1214 overlapping subclones generated a complete 1,900 bp sequence from both strands of the cDNA (Table C). The nucleotide sequence of the coding strand, together with its deduced amino acid sequence, are shown in FIG. 3A and Table D, and a compilation of significant structural features of both amino acid and nucleotide sequences are summarized on the restriction map shown in FIG. 3B.

(i) Open reading frames: Analysis of the compiled nucleotide sequence by the UWGCG program FRAMES revealed the longest open reading frame (ORF) to be 1,248 nt commencing with the ATG at position 73 and terminating at nt 1320 (TAA) of frame 1 as represented in FIG. 3A. The amino acid sequence coded for by this ORF conforms well to coding criteria such as codon utilization, amino acid constituency, and positional base preference as determined by analysis with several different algorithms. The initiator methionine bears a number of the features that seem to characterize the majority of eukaryotic mRNAs sequenced thus far (Kozak, M. [1984] Nucl. Acids Res. 12:857–872). For example, it is the closest to the 5' end of the sequence, conforms perfectly at crucial positions (capitalized below) to the Kozak consensus (ccRccATGG), and is preceded by both in-frame (TAA at −27) and out-frame (TGA at −7) terminators.

(ii) 5' and 3' untranslated regions: Although we have no direct evidence (e.g., from primer extension) to indicate that the 5' non-coding sequence represented by the 72 bp of the cDNA shown in FIG. 3A is complete, both the size of the complementary mRNA on Northern blots (see FIG. 2) and the fact that the cDNA sequence in pcD-1214 begins with a purine, argue in favor of a full-length clone. The 3' non-translated sequence of 580 bp in pcD-1214 contains four AATAAA (underlined in FIG. 3A) consensus polyadenylation signals (Proudfoot, N. J. and Brownlee, G. G. [1976] Nature 263:211–214) in addition to the overlapping pair 17–26 bp proximal to the poly(A) tail in this clone. It appears that certain of these upstream polyadenylation signals in the pcD-1214 gene transcripts may be utilized by some cells as sites for alternate processing of mRNA. Northern blots of THP-1 cell RNA indicate that the processed mRNA for this gene in these monocytic-like cells is approximately 500 nt shorter than the 2 kb species found in monocytes and U937 cells. Interestingly, there is a poly(A) addition signal located at position 1456–1461 in the pcD-1214 nucleotide sequence (see FIG. 3A) that could generated a 1.5 kb mRNA similar to that seen in THP-1 cells.

Another feature of particular interest within the 3'-untranslated region of this clone (positions 1597–1604) is an 8 nt sequence (TTATTTAT) recently reported to be conserved in genes encoding inflammatory mediators, some oncogenes and growth factors (Caput, D., Beutler, B., Hartog, K., Thayer, R., Brown-Shimer, S. and Cerami, A. [1986] Proc. Natl. Acad. Sci. U.S.A. 83:1670–1674). In fact, the degree of homology to tumor necrosis factor (TNFα) mRNA extends to a perfect match over a stretch of 13 nt and there are four flanking, partial repeats (>6 nt homology) of the 8-mer consensus sequence within the 3'-untranslated region of the pcD-1214 cDNA (FIG. 3A). The precise significance of this conserved 3'-sequence is not yet clear, although recent work by Shaw and Kamen (Shaw, G. and Kamen, R. [1986] Cell 46:659–667) suggests that it may be related to mRNA lability and possibly provide a "target" for a specific RNase involved in rapid message turnover.

(iii) Properties of the predicted protein: The nucleotide sequence shown in FIG. 3A can code for a 415 amino acid long polypeptide of 46,596 molecular weight. This polypeptide has a hydrophobic amino terminus (14 of the first 20 amino acids are non-polar), and therefore probably represents the precursor of a secreted protein. A comparison of the amino-terminal sequence of the predicted protein with both the consensus sequences for known signal peptides (Von Heijne, G. [1983] Eur. J. Biochem. 133:17–21) and a putative signal peptidase recognition site (Perlman, D. and Halvorson, H. O. [1983] J. Molec. Biol. 167:391–409), suggests that removal of the leader sequence would occur between the $Ala_{22}$ and $Ser_{23}$ residues of the pcD-1214 polypeptide (filled arrowhead in FIG. 3A). This post-translational processing of the precursor polypeptide would yield an extracellular protein with a molecular weight around 43 kD containing 3 potential sites for N-linked glycosylation (Asn-X-Ser/Thr, where X is not Pro (Bause, E. [1983] Biochem. J. 209:331–336) and four of the five cysteine residues found within the 415 amino acid long precursor polypeptide (see FIGS. 3A and 3B). The net charge of both the predicted precursor and mature polypeptides is −9. Therefore, in the absence of glycosylation, this protein would have an acidic isoelectric point (PI).

(iv) Homology of the predicted protein: A search of the NBRF protein sequence database using the Lipman and Pearson (Lipman, D. J. and Pearson, W. R. [1985] Science 227:1435–1441) algorithm FASTP revealed that the polypeptide encoded by the pcD-1214 clone contained substantial homology to members of the serine protease inhibitor (Serpin) superfamily (Hunt, L. T. and Dayhoff, M. O. [1980] Biochem. Biophys. Res. Commun. 95:864–871). The degree of amino acid homology between the amino acid sequence predicted from the pcD-1214 clone and the Serpins indicated by this preliminary analysis was sufficiently strong (e.g., antithrombin III 33%; ovalbumin 39%; $α_1$-protease inhibitor 31%) to suggest a tentative identification of the pcD-1214 polypeptide as a novel monocyte-derived Serpin. A more stringent assessment of the degree of relatedness between this monocyte Serpin and other human protease inhibitors was obtained by use of the NBRF program ALIGN. FIG. 4 shows the optimized alignments of the carboxyl segments of three human Serpins against the monocyte Serpin. Unlike FASTP, ALIGN takes into account all potential conservative replacements in aligning sequences. Boxed regions in FIG. 4 contain structurally similar amino acids grouped according to the classification of Toh et al. (Toh, H., Hayashida, H. and Miyata, T. [1983] Nature 305:827–829). The degree of sequence relatedness is scored as the number of standard deviation (SD) units the alignment is displaced from an alignment of two sequences following amino acid randomization. The align scores of 16–23 SD obtained (see table in FIG. 4) in this analysis indicate that the probability that the monocyte Serpin is not related to antithrombin III (ATIII), $\alpha_1$-protease inhibitor (API) or endothelial cell plasminogen-activator inhibitor (PAI-1) is much less than 1 in $10^{25}$ (Dayhoff, M.O., Ed. [1979] Atlas of Protein Sequence and Structure, Vol. 5, Suppl. 3, National Biomedical Research Foundation, Washington, D.C.). As indicated in FIG. 4 (open arrow), the high degree of perfect homology around the known reactive center residues in several of these Serpins allowed for classification of the monocyte anti-protease (MAS) as an Arg-Serpin (Carrell and Travis, supra).

EXAMPLE 8

Chromosomal assignment of the monocyte Arg-Serpin gene

Figure 5:
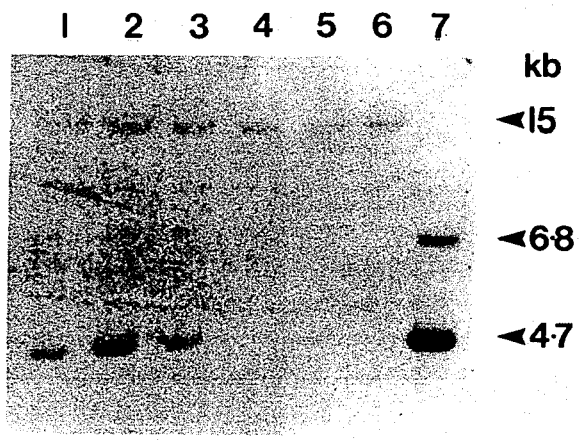
FIG. 5: Southern blot analysis of somatic cell hybrids used in chromosomal assignment of monocyte Arg-Serpin gene. Lanes 1–5: somatic cell hybrid DNAs; Lane 6: mouse genomic DNA; Lane 7: human genomic DNA. Molecular weight markers (right margin) are determined from a λ-HindIII digest run in parallel on the same gel.

Genomic DNA extracted from a series of human-mouse somatic cell hybrids, digested with BglII, was analyzed by Southern blotting for the segregation of the monocyte Arg-Serpin gene with human chromosomes. The blots were probed with the 1256 bp PstI-DraI fragment from pcD-1214. FIG. 5 shows that this probe hybridized strongly under the conditions used to 4.7 and 6.8 kbp BglII fragments of human DNA (lane 7) and cross-hybridized weakly to a 15 kbp mouse fragment (lane 6). Hybrid DNAs that contained both mouse and human sequences complementary to the Arg-Serpin probe (FIG. 5; lanes 1, 2, 3, 5) were readily distinguishable in this analysis from genomic DNA that contained only the mouse gene (lane 4). Data obtained from Southern blot analysis of 32 independent hybrid lines with respect to the segregation of the Arg-Serpin probe and specific human chromosomes allowed the unambiguous assignment of the monocyte Arg-Serpin gene to human chromosome 18.

EXAMPLE 9

In vitro synthesis of monocyte Arg-Serpin polypeptide

In order to confirm the fidelity of the deduced ORF postulated for the monocyte Arg-Serpin encoded within the pcD-1214 cDNA, a subclone containing the SP6 promoter was used to generate in vitro transcripts which were subsequently translated in reticulocyte lysates containing [$^{35}$S]-methionine. This resulted in the synthesis of a predominant, radio-labelled polypeptide with an apparent ($M_r$) of approximately 42,000 when analyzed by SDS-PAGE (FIG. 6). The size of this protein corresponds well to that predicted from the nucleotide sequence (46,596 MW) and is within the accepted limits of variability for SDS-PAGE analysis. The minor species of labelled polypeptides with a smaller $M_r$ seen in this analysis (FIG. 6) probably represent translation products derived from initiation at internal AUG codons with a strong Kozak consensus sequence (−3 purine and G at +4) (Kozak M. [1984] Nucl. Acids Res. 12:857–872) of which there are 6 (amino acid positions 39, 41, 196, 327, 329, 359) within the pcD-1214 transcripts.

EXAMPLE 10

Expression of recombinant PAI-2

The original cDNA clone containing the sequence for the 415 amino acid precursor polypeptide for PAI-2 can be engineered during subcloning into commercial-scale expression vectors to remove the 22 amino acid signal peptide to ensure maximal biological activity. This clone coding for mature PAI-2 protein would therefore be modified to initiate at a methionine (ATG codon) immediately preceding the serine residue at position 23 found in the precursor sequence. Since there are 3 sites within the sequence for potential asparagine-linked glycosylation, it is advantageous to express the protein in yeast or mammalian cells to obtain fully-active, stable protein. With the recognition of a nucleotide sequence in the 3' untranslated region (positions 1597–1604) of pcD-1214 that confers instability on mRNAs that contain it (Shaw, G. and Kamen, R. [1986] Cell 46:659–667), it may also be desirable to delete this sequence to maximize PAI-2 mRNA stability for efficient protein production.

EXAMPLE 11

Prevention of tumor cell infiltration and metastasis

Localized proteolytic destruction of connective tissue is generally considered as a prerequisite for tumor cell invasion. Secretion of plasminogen-activator (PA) by endothelial cells, leading to production of plasmin, has been proposed as a mechanism for initiating this process (Ossowski, L. and Reich, E. [1983] Cell 35:611–619). The onset of PA synthesis has also been associated with a variety of neoplasia (Unkeless, J.C., Gordon, S. and Reich, E. [1974] J. Exp. Med. 139:834–850; Markus, G., Takita, H., Camiolo, S.M., Corasanti, J.G., Evers, J.L. and Hobika, G.H. [1980] Cancer Res. 40:841–848). Antibodies directed to PA have been shown to inhibit tumor cell metastasis (Ossowski, L. and Reich, E., supra; Mignatti, P., Robbins, E. and Rifkin, D.B. [1986] Cell 47:487–498). It is reasonable to assume that inhibitors of PA, such as the one coded for by plasmid pcD-1214, will inhibit both tumor metastasis and growth (Dvorak, H.F. [1986] New Eng. Journ. of Med. 315:1650–1659).

EXAMPLE 12

Control of fibrinolysis

The destruction of blood clots is mediated by plasmin breakdown of fibrin (i.e., fibrinolysis). The inactive plasminogen is converted to plasmin by the action of PA and then fibrinolysis is normally terminated by inhibition of plasmin by anti-plasmin. There are clinical disorders caused either by genetic or disease-related defects in the fibrinolytic inhibitors, or as a side-effect of therapeutic administration of fibrinolytic agents. Presently, these conditions of excessive fibrinolysis, or bleeding, are controlled by administration of ε-aminocaproic acid (EACA), which prevents the binding of plasmin to fibrin (Marder, V.J. and Francis, C.W. [1983] in Hematology (3rd ed.), Williams, W.J., Beutler, E., Erslev, A.J. and Lichtman, M.A., Ed., pp. 1462–1473, McGraw-Hill Book Co., N.Y.). However, the use of EACA is not without its side-effects and the control of fibrinolysis by administration of PAI-2 would provide a more physiological alternative to this therapy.

The cloning vehicle of the subject invention is used to make available for the first time, and to increase the supply of, the gene coding for PAI-2 by replication of a transformed host. Expected levels of PAI-2 expression will make essentially pure PAI-2 available at a more economical cost.

The PAI-2 gene can be used as a probe to locate the gene coding for a PAI-2, or PAI-2-like activity, in mammals and other animals. Further, the PAI-2 of the subject invention can be used to give rise to antibodies, e.g., monoclonal and polyclonal antibodies, which can be used in diagnostic assays, or for other purposes relating to the identification of PAI-2 present in serum or other clinical specimens.

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
|---|---|---|---|
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T
QR = AG if S is T or C
J = A or G
K = T or C
L = A, T, C or G
M = A, C or T The above shows that the novel amino acid sequence of PAI-2 can be prepared by nucleotide sequences other than that in clone pcD-1214. Functionally equivalent nucleotide sequences encoding the novel amino acid sequence of PAI-2, or fragments thereof having plasminogen activator inhibitor activity, can be prepared by known synthetic procedures. Accordingly, the subject invention includes such functionally equivalent nucleotide sequences.

The one-letter symbol for the amino acids used in Table B is well known in the art. For convenience, the relationship of the three-letter abbreviation and the one-letter symbol for amino acids is as follows: Ala (A), Arg (R), Asn (N), Asp (D), Cys (C), Gln (Q) Glu (E), Gly (G), His (H), Ile (I), Leu (L), Lys (K), Met (M), Phe (F), Pro (P), Ser (S), Thr (T), Trp (W), Tyr (Y), and Val (V).

Thus, the scope of the subject invention includes not only the specific nucleotide sequences depicted herein, which are in the essentially pure form substantially free of other DNA, but also all equivalent nucleotide sequences coding for molecules with substantially the same PAI-2 biological activity. The term "equivalent" is being used in its ordinary patent usage here as denoting a nucleotide sequence which performs substantially as the nucleotide sequence identified herein to produce molecules with substantially the same PAI-2 biological activity in essentially the same kind of hosts. Within this definition are sub-fragments which have PAI-2 biological activity.

It is well within the skill of those in the genetic engineering art to use the nucleotide sequences encoding precursor or mature PAI-2 of the subject invention to produce PAI-2 via microbial processes. Fusing the sequences into an expression vector and transforming or transfecting into hosts, either eukaryotic (yeast or mammalian cells) or prokaryotic (bacterial cells), are standard procedures used in producing other well-known proteins, e.g., insulin, interferons, human growth hormone, and the like. Similar procedures, or obvious modifications thereof, can be employed to prepare PAI-2 proteins by microbial means or mammalian tissue-culture technology in accord with the subject invention.

In addition, it has been shown that proteins of identified structure and function may be constructed by changing the amino acid sequence if such changes do not alter the protein secondary structure (Kaiser, E.T. and Kezdy, F.J. [1984] Science 223:249–255). Thus, the subject invention includes mutenes (mutants) of the amino acid sequences depicted herein which do not alter the protein secondary structure.

The subject invention also includes serpins having changes in amino acids within the boxed regions shown in FIG. 4. These regions are conserved between the two different PAI sequences, i.e., PAI-1 and PAI-2. It is well within the skill of persons in molecular biology to use standard site-directed mutagenesis to effect amino acid changes, deletion(s) or substitution(s), in these conserved regions. These changed PAIs can be expected to have comparable or enhanced PAI activity in comparison with the parent sequences. Further, these PAIs can be used for the same purposes as PAI-2.

The work described herein was all done in conformity with physical and biological containment requirements specified in the NIH Guidelines.

TABLE A

| Amino Acid Sequence of Precursor PAI-2 | | | | | | | | | | | | | | | | | |
|---|---|---|---|---|---|---|---|---|---|---|---|---|---|---|---|---|---|
| 1 | | M | E | D | L | C | V | A | N | T | L | F | A | L | N | L | F | 16 |
| 17 | K | H | L | A | K | A | S | P | T | Q | N | L | F | L | S | P | W | S | I | S | 36 |

TABLE A-continued

Amino Acid Sequence of Precursor PAI-2

| | | | | | | | | | | | | | | | | | | | | |
|---|---|---|---|---|---|---|---|---|---|---|---|---|---|---|---|---|---|---|---|---|
| 37 | S | T | M | A | M | V | Y | M | G | S | R | G | S | T | E | D | Q | M | A | K | 56 |
| 57 | V | L | Q | F | N | E | V | G | A | N | A | V | T | P | M | T | P | E | N | F | 76 |
| 77 | T | S | C | G | F | M | Q | Q | I | Q | K | G | S | Y | P | D | A | I | L | Q | 96 |
| 97 | A | Q | A | A | D | K | I | H | S | S | F | R | S | L | S | S | A | I | N | A | 116 |
| 117 | S | T | G | N | Y | L | L | E | S | V | N | K | L | F | G | E | K | S | A | S | 136 |
| 137 | F | R | E | E | Y | I | R | L | C | Q | K | Y | Y | S | S | E | P | Q | A | V | 156 |
| 157 | D | F | L | E | C | A | E | E | A | R | K | K | I | N | S | W | V | K | T | Q | 176 |
| 177 | T | K | G | K | I | P | N | L | L | P | E | G | S | V | D | G | D | T | R | M | 196 |
| 197 | V | L | V | N | A | V | Y | F | K | G | K | W | K | T | P | F | E | K | K | L | 216 |
| 217 | N | G | L | Y | P | F | R | V | N | S | A | Q | R | T | P | V | Q | M | M | Y | 236 |
| 237 | L | R | E | K | L | N | I | G | Y | I | E | D | L | K | A | Q | I | L | E | L | 256 |
| 257 | P | Y | A | G | D | V | S | M | F | L | L | L | P | D | E | I | A | D | V | S | 276 |
| 277 | T | G | L | E | L | L | E | S | E | I | T | Y | D | K | L | N | K | W | T | S | 296 |
| 297 | K | D | K | M | A | E | D | E | V | E | V | Y | I | P | Q | F | K | L | E | E | 316 |
| 317 | H | Y | E | L | R | S | I | L | R | S | M | G | M | E | D | A | F | N | K | G | 336 |
| 337 | R | A | N | F | S | G | M | S | E | R | N | D | L | F | L | S | E | V | F | H | 356 |
| 357 | Q | A | M | V | D | V | N | E | E | G | T | E | A | A | A | G | T | G | G | V | 376 |
| 377 | M | T | G | R | T | G | H | G | G | P | Q | F | V | A | D | H | P | F | L | F | 396 |
| 397 | L | I | M | H | K | I | T | N | C | I | L | F | F | G | R | F | S | S | P | | 415 |

TABLE B

Amino Acid Sequence of Mature PAI-2

| | | | | | | | | | | | | | | | | | | | | |
|---|---|---|---|---|---|---|---|---|---|---|---|---|---|---|---|---|---|---|---|---|
| 23 | | | | | | | | | | | | | S | P | T | Q | N | L | F | L | S | P | W | S | I | S | 36 |
| 37 | S | T | M | A | M | V | Y | M | G | S | R | G | S | T | E | D | Q | M | A | K | 56 |
| 57 | V | L | Q | F | N | E | V | G | A | N | A | V | T | P | M | T | P | E | N | F | 76 |
| 77 | T | S | C | G | F | M | Q | Q | I | Q | K | G | S | Y | P | D | A | I | L | Q | 96 |
| 97 | A | Q | A | A | D | K | I | H | S | S | F | R | S | L | S | S | A | I | N | A | 116 |
| 117 | S | T | G | N | Y | L | L | E | S | V | N | K | L | F | G | E | K | S | A | S | 136 |
| 137 | F | R | E | E | Y | I | R | L | C | Q | K | Y | Y | S | S | E | P | Q | A | V | 156 |
| 157 | D | F | L | E | C | A | E | E | A | R | K | K | I | N | S | W | V | K | T | Q | 176 |
| 177 | T | K | G | K | I | P | N | L | L | P | E | G | S | V | D | G | D | T | R | M | 196 |
| 197 | V | L | V | N | A | V | Y | F | K | G | K | W | K | T | P | F | E | K | K | L | 216 |
| 217 | N | G | L | Y | P | F | R | V | N | S | A | Q | R | T | P | V | Q | M | M | Y | 236 |
| 237 | L | R | E | K | L | N | I | G | Y | I | E | D | L | K | A | Q | I | L | E | L | 256 |
| 257 | P | Y | A | G | D | V | S | M | F | L | L | L | P | D | E | I | A | D | V | S | 276 |
| 277 | T | G | L | E | L | L | E | S | E | I | T | Y | D | K | L | N | K | W | T | S | 296 |
| 297 | K | D | K | M | A | E | D | E | V | E | V | Y | I | P | Q | F | K | L | E | E | 316 |
| 317 | H | Y | E | L | R | S | I | L | R | S | M | G | M | E | D | A | F | N | K | G | 336 |
| 337 | R | A | N | F | S | G | M | S | E | R | N | D | L | F | L | S | E | V | F | H | 356 |
| 357 | Q | A | M | V | D | V | N | E | E | G | T | E | A | A | A | G | T | G | G | V | 376 |
| 377 | M | T | G | R | T | G | H | G | G | P | Q | F | V | A | D | H | P | F | L | F | 396 |
| 397 | L | I | M | H | K | I | T | N | C | I | L | F | F | G | R | F | S | S | P | | 415 |

TABLE C

Nucleotide Sequence of Monocyte cDNA pcD-1214

| | |
|---|---|
| 1   ACAACTCTCAGAGGAGCATTGCCCGTCAGACAGCAACTCAGAGAATAACCAGAGAACAAC | 60 |
| 61  CAGATTGAAACAATGGAGGATCTTTGTGTGGCAAACACACTCTTTGCCCTCAATTTATTC | 120 |
| 121 AAGCATCTGGCAAAAGCAAGCCCCACCCAGAACCTCTTCCTCTCCCCATGGAGCATCTCG | 180 |
| 181 TCCACCATGGCCATGGTCTACATGGGCTCCAGGGGCAGCACCGAAGACCAGATGGCCAAG | 240 |
| 241 GTGCTTCAGTTTAATGAAGTGGGAGCCAATGCAGTTACCCCCATGACTCCAGAGAACTTT | 300 |
| 301 ACCAGCTGTGGGTTCATGCAGCAGATCCAGAAGGGTAGTTATCCTGATGCGATTTTGCAG | 360 |
| 361 GCACAAGCTGCAGATAAAATCCATTCATCCTTCCGCTCTCTCAGCTCTGCAATCAATGCA | 420 |
| 421 TCCACAGGGAATTATTTACTGGAAAGTGTCAATAAGCTGTTTGGTGAGAAGTCTGCGAGC | 480 |
| 481 TTCCGGGAAGAATATATTCGACTCTGTCAGAAATATTACTCCTCAGAACCCCAGGCAGTA | 540 |
| 541 GACTTCCTAGAATGTGCAGTGGGAGCCAATGCAGTTACCCCCATGACTCCAGAGAACTTT | 600 |
| 601 ACCAAAGGCAAAATCCCAAACTTGTTACCTGAAGGTTCTGTAGATGGGGATACCAGGATG | 660 |

TABLE C-continued
Nucleotide Sequence of Monocyte cDNA pcD-1214

| | |
|---|---|
| 661 GTCCTGGTGAATGCTGTCTACTTCAAAGGAAAGTGGAAAACTCCATTTGAGAAGAAACTA | 720 |
| 721 AATGGGCTTTATCCTTTCCGTGTAAACTCGGCTCAGCGCACACCTGTACAGATGATGTAC | 780 |
| 781 TTGCGTGAAAAGCTAAACATTGGATACATAGAAGACCTAAAGGCTCAGATTCTAGAACTC | 840 |
| 841 CCATATGCTGCATGTTCTTGCATGTTCTTGTTGCTTCCAGATGAAATTGCCGATGTGTCC | 900 |
| 901 ACTGGCTTGGAGCTGCTGGAAAGTGAAATAACCTATGACAAACTCAACAAGTGGACCAGC | 960 |
| 961 AAAGACAAAATGGCTGAAGATGAAGTTGAGGTATACATACCCCAGTTCAAATTAGAAGAG | 1020 |
| 1021 CATTATGAACTCAGATCCATTCTGAGAAGCATGGGCATGGAGGACGCCTTCAACAAGGGA | 1080 |
| 1081 CGGGCCAATTTCTCAGGGATGTCGGAGAGGAATGACCTGTTTCTTTCTGAAGTGTTCCAC | 1140 |
| 1141 CAAGCCATGGTGGATGTGAATGAGGAGGGCACTGAAGCAGCCGCTGGCACAGGAGGTGTT | 1200 |
| 1201 ATGACAGGGAGAACTGGACATGGAGGCCCACAGTTTGTGGCAGATCATCCTTTTCTTTTT | 1260 |
| 1261 CTTATTATGCATAAGATAACCAACTGCATTTTATTTTTCGGCAGATTTTCCTCACCCTAA | 1320 |
| 1321 AACTAAGCGTGCTGCTTCTGCAAAAGATTTTTGTAGATGAGCTGTGTGCCTCAGAATTGC | 1380 |
| 1381 TATTTCAAATTGCCAAAAATTTAGAGATGTTTTCTACATATTTCTGCTCTTCTGAACAAC | 1440 |
| 1441 TTCTGCTACCCACTAAATAAAAACACAGAAATAATTAGACAATTGTCTATTATAACATGA | 1500 |
| 1501 CAACCCTATTAATCATTTGGTCTTCTAAAATGGGATCATGCCCATTTAGATTTTCCTTAC | 1560 |
| 1561 TATCAGTTTATTTTTATAACATTAACTTTTACTTTGTTATTTATTATTTTATATAATGGT | 1620 |
| 1621 GAGTTTTTAAATTATTGCTCACTGCCTATTTAATGTAGCTAATAAAGTTATAGAAGCAGA | 1680 |
| 1681 TGATCTGTTAATTTCCTATCTAATAAATGCCTTTAATTGTTCTCATAATGAAGAATAAGT | 1740 |
| 1741 AGGTACCCTCCATGCCCTTCTGTAATAAATATCTGGAAAAAACATTAAACAATAGGCAAA | 1800 |
| 1801 TATATGTTATGTGCATTTCTAGAAATACATAACACATATATATGTCTGTATCTTATATTC | 1860 |
| 1861 AATTGCAAGTATATAATAAATAAACCTGCTTCCAAACAACAAAAAAAAAAAAAAAAAAAA | 1920 |

TABLE D
Nucleotide Sequence and Deduced Amino Acid Sequence of pcD-1214

| | |
|---|---|
| 1 ACAACTCTCAGAGGAGCATTGCCCGTCAGACAGCAACTCAGAGAATAACCAGAGAACAAC | 60 |
| 61 CAGATTGAAACAATGGAGGATCTTTGTGTGGCAAACACACTCTTTGCCCTCAATTTATTC<br>1                      M  E  D  L  C  V  A  N  T  L  F  A  L  N  L  F | 120<br>16 |
| 121 AAGCATCTGGCAAAAGCAAGCCCCACCCAGAACCTCTTCCTCTCCCCATGGAGCATCTCG<br>17 K  H  L  A  K  A  S  P  T  Q  N  L  F  L  S  P  W  S  I  S | 180<br>36 |
| 181 TCCACCATGGCCATGGTCTACATGGGCTCCAGGGGCAGCACCGAAGACCAGATCGCCAAG<br>37 S  T  M  A  M  V  Y  M  G  S  R  G  S  T  E  D  Q  M  A  K | 240<br>56 |
| 241 GTGCTTCAGTTTAATGAAGTGGGAGCCAATGCAGTTACCCCCATGACTCCAGAGAACTTT<br>57 V  L  Q  F  N  E  V  G  A  N  A  V  T  P  M  T  P  E  N  F | 300<br>76 |

TABLE D-continued
Nucleotide Sequence and Deduced Amino Acid Sequence of pcD-1214

```
301 ACCAGCTGTGGGTTCATGCAGCAGATCCAGAAGGGTAGTTATCCTGATGCGATTTTGCAG      360
 77  T   S   C   G   F   M   Q   Q   I   Q   K   G   S   Y   P   D   A   I   L   Q       96

361 GCACAAGCTGCAGATAAAATCCATTCATCCTTCCGCTCTCTCAGCTCTGCAATCAATGCA      420
 97  A   Q   A   A   D   K   I   H   S   S   F   R   S   L   S   S   A   I   N   A      116

421 TCCACAGGGAATTATTTACTGGAAAGTGTCAATAAGCTGTTTGGTGAGAAGTCTGCGAGC      480
117  S   T   G   N   Y   L   L   E   S   V   N   K   L   F   G   E   K   S   A   S      136

481 TTCCGGGAAGAATATAYYCGACTCTGTCAGAAATATTACTCCTCAGAACCCCAGGCAGTA      540
137  F   R   E   E   Y   I   R   L   C   Q   K   Y   Y   S   S   E   P   Q   A   V      156

541 GACTTCCTAGAATGTGCAGAAGAAGCTAGAAAAAAGATTAATTCCTGGGTCAAGACTCAA      600
157  D   F   L   E   C   A   E   E   A   R   K   K   I   N   S   W   V   K   T   Q      176

601 ACCAAAGGCAAAATCCCAAACTTGTTACCTGAAGGTTCTGTAGATGGGGATACCAGGATG      660
177  T   K   G   K   I   P   N   L   L   P   E   G   S   V   D   G   D   T   R   M      196

661 GTCCTGGTGAATGCTGTCTACTTCAAAGGAAAGTGGAAAACTCCATTTGAGAAGAAACTA      720
197  V   L   V   N   A   V   Y   F   K   G   K   W   K   T   P   F   E   K   K   L      216

721 AATGGGCTTTATCCTTTCCGTGTAAACTCGGCTCAGCGCACACCTGTACAGATGATGTAC      780
217  N   G   L   Y   P   F   R   V   N   S   A   Q   R   T   P   V   Q   M   M   Y      236

781 TTGCGTGAAAAGCTAAACATTGGATACATAGAAGACCTAAAGGCTCAGATTCTAGAACTC      840
237  L   R   E   K   L   N   I   G   Y   I   E   D   L   K   A   Q   I   L   E   L      256

841 CCATATGCTGGAGATGTTAGCATGTTCTTGTTGCTTCCAGATGAAATTGCCGATGTGTCC      900
257  P   Y   A   G   D   V   S   M   F   L   L   L   P   D   E   I   A   D   V   S      276

901 ACTGGCTTGGAGCTGCTGGAAAGTGAAATAACCTATGACAAACTCAACAAGTGGACCAGC      960
277  T   G   L   E   L   L   E   S   E   I   T   Y   D   K   L   N   K   W   T   S      296

961 AAAGACAAAATGGCTGAAGATGAAGTTGAGGTATACATACCCCAGTTCAAATTAGAAGAG     1020
297  K   D   K   M   A   E   D   E   V   E   V   Y   I   P   Q   F   K   L   E   —      316

1021 CATTATGAACTCAGATCCATTCTGAGAAGCATGGGCATGGAGGACGCCTTCAACAAGGGA     1080
317  H   Y   E   L   R   S   I   L   R   S   M   G   M   E   D   A   F   N   K   G      336

1081 CGGGCCAATTTCTCAGGGATGTCGGAGAGGAATGACCTGTTTCTTTCTGAAGTGTTCCAC     1140
337  R   A   N   F   S   G   M   S   E   R   N   D   L   F   L   S   E   V   F   H      356

1141 CAAGCCATGGTGGATGTGAATGAGGAGGGCACTGAAGCAGCCGCTGGCACAGGAGGTGTT     1200
357  Q   A   M   V   D   V   N   E   E   G   T   E   A   A   A   G   T   G   G   V      376

1201 ATGACAGGGAGAACTGGACATGGAGGCCCACAGTTTGTGGCAGATCATCCTTTTCTTTTT     1260
377  M   T   G   R   T   G   H   G   G   P   Q   F   V   A   D   H   P   F   L   F      396

1261 CTTATTATGCATAAGATAACCAACTGCATTTTATTTTTCGGCAGATTTTCCTCACCCTAA     1320
397  L   I   M   H   K   I   T   N   C   I   L   F   F   G   R   F   S   S   P           415

1321 AACTAAGCGTGCTGCTTCTGCAAAAGATTTTTGTAGATGAGCTGTGTGCCTCAGAATTGC     1380

1381 TATTTCAAATTGCCAAAAATTTAGAGATGTTTTCTACATATTTCTGCTCTTCTGAACAAC     1440

1441 TTCTGCTACCCACTAAATAAAAACACAGAAATAATTAGACAATTGTCTATTATAACATGA     1500

1501 CAACCCTATTAATCATTTGGTCTTCTAAAATGGGATCATGCCCATTTAGATTTTCCTTAC     1560

1561 TATCAGTTTATTTTTATAACATTAACTTTTACTTTGTTATTTATTATTTTATATAATGGT     1620

1621 GAGTTTTTAAATTATTGCTCACTGCCTATTTAATGTAGCTAATAAAGTTATAGAAGCAGA     1680
```

TABLE D-continued

Nucleotide Sequence and Deduced Amino Acid Sequence of pcD-1214

```
1681 TGATCTGTTAATTTCCTATCTAATAAATGCCTTTAATTGTTCTCATAATGAAGAATAAGT    1740

1741 AGGTACCCTCCATGCCCTTCTGTAATAAATATCTGGAAAAAACATTAAACAATAGGCAAA    1800

1801 TATATGTTATGTGCATTTCTAGAAATACATAACACATATATATGTCTGTATCTTATATTC    1860

1861 AATTGCAAGTATATAATAAATAAACCTGCTTCCAAACAACAAAAAAAAAAAAAAAAAAAA    1920
```

We claim:

1. Recombinant DNA coding for human precursor PAI-2 comprising the following amino acid sequence:

| 1 | M E D L C V A N T L F A L N L F | 16 |
|---|---|---|
| 17 | K H L A K A S P T Q N L F L S P W S I S | 36 |
| 37 | S T M A M V Y M G S R G S T E D Q M A K | 56 |
| 57 | V L Q F N E V G A N A V T P M T P E N F | 76 |
| 77 | T S C G F M Q Q I Q K G S Y P D A I L Q | 96 |
| 97 | A Q A A D K I H S S F R S L S S A I N A | 116 |
| 117 | S T G N Y L L E S V N K L F G E K S A S | 136 |
| 137 | F R E E Y I R L C Q K Y Y S S E P Q A V | 156 |
| 157 | D F L E C A E E A R K K I N S W V K T Q | 176 |
| 177 | T K G K I P N L L P E G S V D G D T R M | 196 |
| 197 | V L V N A V Y F K G K W K T P F E K K L | 216 |
| 217 | N G L Y P F R V N S A Q R T P V Q M M Y | 236 |
| 237 | L R E K L N I G Y I E D L K A Q I L E L | 256 |
| 257 | P Y A G D V S M F L L L P D E I A D V S | 276 |
| 277 | T G L E L L E S E I T Y D K L N K W T S | 296 |
| 297 | K D K M A E D E V E V Y I P Q F K L E E | 316 |
| 317 | H Y E L R S I L R S M G M E D A F N K G | 336 |
| 337 | R A N F S G M S E R N D L F L S E V F H | 356 |
| 357 | Q A M V D V N E E G T E A A A G T G G V | 376 |
| 377 | M T G R T G H G G P Q F V A D H P F L F | 396 |
| 397 | L I M H K I T N C I L F F G R F S S P. | 415 |

2. A DNA transfer vector comprising a gene coding for human precursor PAI-2 comprising the following amino acid sequence:

| 1 | M E D L C V A N T L F A L N L F | 16 |
|---|---|---|
| 17 | K H L A K A S P T Q N L F L S P W S I S | 36 |
| 37 | S T M A M V Y M G S R G S T E D Q M A K | 56 |
| 57 | V L Q F N E V G A N A V T P M T P E N F | 76 |
| 77 | T S C G F M Q Q I Q K G S Y P D A I L Q | 96 |
| 97 | A Q A A D K I H S S F R S L S S A I N A | 116 |
| 117 | S T G N Y L L E S V N K L F G E K S A S | 136 |
| 137 | F R E E Y I R L C Q K Y Y S S E P Q A V | 156 |
| 157 | D F L E C A E E A R K K I N S W V K T Q | 176 |
| 177 | T K G K I P N L L P E G S V D G D T R M | 196 |
| 197 | V L V N A V Y F K G K W K T P F E K K L | 216 |
| 217 | N G L Y P F R V N S A Q R T P V Q M M Y | 236 |
| 237 | L R E K L N I G Y I E D L K A Q I L E L | 256 |
| 257 | P Y A G D V S M F L L L P D E I A D V S | 276 |
| 277 | T G L E L L E S E I T Y D K L N K W T S | 296 |
| 297 | K D K M A E D E V E V Y I P Q F K L E E | 316 |
| 317 | H Y E L R S I L R S M G M E D A F N K G | 336 |
| 337 | R A N F S G M S E R N D L F L S E V F H | 356 |
| 357 | Q A M V D V N E E G T E A A A G T G G V | 376 |
| 377 | M T G R T G H G G P Q F V A D H P F L F | 396 |
| 397 | L I M H K I T N C I L F F G R F S S P. | 415 |

3. The DNA transfer vector of claim 2, transferred to and replicated in a prokaryotic or eukaryotic host.

4. Plasmid pcD-1214, a transfer vector according to claim 3.

5. A DNA transfer vector comprising a gene coding for human mature PAI-2 containing DNA encoding methionine immediately preceding the serine residue at position 23 in the precursor PAI-2 DNA sequence.

6. A mammalian tissue culture cell transfected by the transfer vector of claim 2 or 5.

7. A yeast transformed by the transfer vector of claim 2 or 5.

8. Recombinant DNA coding for human mature PAI-2 comprising the following amino acid sequence:

| 23 | S P T Q N L F L S P W S I S | 36 |
|---|---|---|
| 37 | S T M A M V Y M G S R G S T E D Q M A K | 56 |
| 57 | V L Q F N E V G A N A V T P M T P E N F | 76 |
| 77 | T S C G F M Q Q I Q K G S Y P D A I L Q | 96 |
| 97 | A Q A A D K I H S S F R S L S S A I N A | 116 |
| 117 | S T G N Y L L E S V N K L F G E K S A S | 136 |
| 137 | F R E E Y I R L C Q K Y Y S S E P Q A V | 156 |
| 157 | D F L E C A E E A R K K I N S W V K T Q | 176 |
| 177 | T K G K I P N L L P E G S V D G D T R M | 196 |
| 197 | V L V N A V Y F K G K W K T P F E K K L | 216 |
| 217 | N G L Y P F R V N S A Q R T P V Q M M Y | 236 |
| 237 | L R E K L N I G Y I E D L K A Q I L E L | 256 |
| 257 | P Y A G D V S M F L L L P D E I A D V S | 276 |
| 277 | T G L E L L E S E I T Y D K L N K W T S | 296 |
| 297 | K D K M A E D E V E V Y I P Q F K L E E | 316 |
| 317 | H Y E L R S I L R S M G M E D A F N K G | 336 |
| 337 | R A N F S G M S E R N D L F L S E V F H | 356 |
| 357 | Q A M V D V N E E G T E A A A G T G G V | 376 |
| 377 | M T G R T G H G G P Q F V A D H P F L F | 396 |
| 397 | L I M H K I T N C I L F F G R F S S P. | 415 |

9. A DNA transfer vector comprising a gene coding for human mature PAI-2 in association with a signal peptide sequence, wherein said gene comprises DNA coding for the following amino acid sequence:

| 23 | S P T Q N L F L S P W S I S | 36 |
|---|---|---|
| 37 | S T M A M V Y M G S R G S T E D Q M A K | 56 |
| 57 | V L Q F N E V G A N A V T P M T P E N F | 76 |
| 77 | T S C G F M Q Q I Q K G S Y P D A I L Q | 96 |
| 97 | A Q A A D K I H S S F R S L S S A I N A | 116 |
| 117 | S T G N Y L L E S V N K L F G E K S A S | 136 |
| 137 | F R E E Y I R L C Q K Y Y S S E P Q A V | 156 |
| 157 | D F L E C A E E A R K K I N S W V K T Q | 176 |
| 177 | T K G K I P N L L P E G S V D G D T R M | 196 |
| 197 | V L V N A V Y F K G K W K T P F E K K L | 216 |
| 217 | N G L Y P F R V N S A Q R T P V Q M M Y | 236 |
| 237 | L R E K L N I G Y I E D L K A Q I L E L | 256 |
| 257 | P Y A G D V S M F L L L P D E I A D V S | 276 |
| 277 | T G L E L L E S E I T Y D K L N K W T S | 296 |
| 297 | K D K M A E D E V E V Y I P Q F K L E E | 316 |
| 317 | H Y E L R S I L R S M G M E D A F N K G | 336 |
| 337 | R A N F S G M S E R N D L F L S E V F H | 356 |
| 357 | Q A M V D V N E E G T E A A A G T G G V | 376 |
| 377 | M T G R T G H G G P Q F V A D H P F L F | 396 |
| 397 | L I M H K I T N C I L F F G R F S S P. | 415 |

10. The DNA transfer vector of claim 9, transferred to and replicated in a prokaryotic or eukaryotic host.

11. A process for preparing PAI-2 which comprises culturing a prokaryotic or eukaryotic host hosting a recombinant DNA transfer vector comprising DNA coding for PAI-2.

12. A process, according to claim 11, wherein said transfer vector is pcD-1214.

13. The microorganism *E. coli* HB101(pcD-1214).

* * * * *

UNITED STATES PATENT AND TRADEMARK OFFICE
CERTIFICATE OF CORRECTION

PATENT NO.    :   4,923,807

DATED         :   May 8, 1990

INVENTOR(S)   :   Webb et al.

It is certified that error appears in the above-identified patent and that said Letters Patent is hereby corrected as shown below:

| | |
|---|---|
| Column 7: | line 7-8: "E. coli" should read --E. coli--; line 24: "E. coli" should read --E. coli--. |
| Column 13: | line 61: "M-A, C or T" should read --M=A, C or T--. |
| Column 15: | Table C, line 541: "GACTTCCTAGAATGTG CAGTGGGAGCCAATGCAGTTACCCCCATGACTCC AGAGAACTTT" should read --GACTTCCTAG AATGTGCAGAAGAAGCTAGAAAAAGATTAATTC CTGGGTCAAGACTCAA--. |
| Column 17: | Table C, line 841: "CCATATGGTGCATGTTCTTG" should read --CCATATGCTGGAGATGTTAG--. |
| Column 18: | Table D, line 181: "AGATCGCCAAG" should read --AGATGGCCAAG--. |
| Column 19: | Table D, line 481: "TTCCGGGAAGAATATAYYCG" should read --TTCCGGGAAGAATATATTCG--. |

Signed and Sealed this

Twelfth Day of January, 1993

Attest:

DOUGLAS B. COMER

*Attesting Officer*   *Acting Commissioner of Patents and Trademarks*